(12) United States Patent
Yu et al.

(10) Patent No.: US 11,467,154 B2
(45) Date of Patent: Oct. 11, 2022

(54) OPTICAL NANO-BIOSENSING SYSTEM AND METHOD THEREOF

(71) Applicant: National Chung Cheng University, Chia-Yi (TW)

(72) Inventors: Sung-Nien Yu, Minxiong Township (TW); Tsung-Heng Tsai, Chiayi (TW); Lai-Kwan Chau, Chiayi (TW)

(73) Assignee: National Chung Cheng University, Chia-Yi (TW)

( * ) Notice: Subject to any disclaimer, the term of this patent is extended or adjusted under 35 U.S.C. 154(b) by 478 days.

(21) Appl. No.: 16/782,745

(22) Filed: Feb. 5, 2020

(65) Prior Publication Data
US 2021/0011011 A1 Jan. 14, 2021

(30) Foreign Application Priority Data
Jul. 11, 2019 (TW) ................. 108124548

(51) Int. Cl.
*G01N 33/543* (2006.01)
*H03M 1/12* (2006.01)
*B01L 3/00* (2006.01)

(52) U.S. Cl.
CPC .. *G01N 33/54346* (2013.01); *B01L 3/502715* (2013.01); *H03M 1/12* (2013.01); *B01L 2300/0636* (2013.01)

(58) Field of Classification Search
CPC ............ G01N 33/54346; G01N 21/554; B01L 3/502715; B01L 2300/0636; H03M 1/12
See application file for complete search history.

(56) References Cited

U.S. PATENT DOCUMENTS

| 2010/0086992 | A1 | 4/2010 | Himmelhaus et al. |
| 2010/0123900 | A1* | 5/2010 | Chau ................... G01N 21/554 977/810 |
| 2013/0231574 | A1 | 9/2013 | Tran |

OTHER PUBLICATIONS

Notice of Office Action of corresponding TW application 108124548, published on Feb. 4, 2020.

* cited by examiner

*Primary Examiner* — Jennifer Wecker
*Assistant Examiner* — Oyeleye Alexander Alabi
(74) *Attorney, Agent, or Firm* — Wang Law Firm, Inc.

(57) ABSTRACT

An optical nano-biosensing system and a method thereof are provided. The optical nano-biosensing system includes a nano-plasmonic sensing device, a high-resolution analog-to-digital converter, a signal acquisition and processing device, and an intelligent electronic device. The nano-plasmonic sensing device further includes a light-source control circuit, a sample receiver, a light detector, and a signal-amplifying circuit. The sample receiver receives a sample. The light-source control circuit generates an incident light from a light source to be projected onto the sample receiver. The light detector detects an emergent light from the sample receiver to generate a detection signal. The signal-amplifying circuit converts the detection signal to generate an amplified signal. The high-resolution analog-to-digital converter digitizes the amplified signal to generate a digital signal. The signal calculator of the signal acquisition and processing device operates the digital signal to generate calculated information.

18 Claims, 11 Drawing Sheets

OPTICAL NANO-BIOSENSING SYSTEM AND METHOD THEREOF

CROSS-REFERENCE TO RELATED APPLICATION

This application claims priority from Taiwan Patent Application No. 108124548, filed on Jul. 11, 2019, in the Taiwan Intellectual Property Office, the content of which is hereby incorporated by reference in its entirety for all purposes.

BACKGROUND OF THE INVENTION

1. Field of the Invention

The present invention relates to a biosensing system and method thereof, more particularly to an optical nano-biosensing system and method thereof.

2. Description of the Related Art

Biological sensing analysis is a new analytical technique, and the detection principle thereof is to detect the interaction between immobilized biomolecules and analyte molecules by using the immobilized biomolecules combined with signal transduction elements. The current structure of conventional nano-plasmonic biosensing platforms typically involves the immobilization of recognition molecules on the surface of noble metal nanoparticles, so that the recognition molecules on the surface of the noble metal nanoparticles can interact with an analyte selectively. As the recognition molecules on the noble metal nanoparticles bind with the analyte, the local refractive index at the surface of the noble metal nanoparticles changes, and hence the optical properties of the noble metal nanoparticles such as absorption and scattering cross-sections change correspondingly, thus being able to construct a nano-plasmonic biosensing platform with selectivity by this feature.

For some conventional optical biosensors that utilize noble metal nanostructures, an optical signal variation due to nano-plasmonic resonance signal is amplified by a current amplifier, and the nano-plasmonic resonance variation signal is then converted into a digital signal by an analog-to-digital converter. The nano-plasmonic resonance signal is further analyzed by a computer device. However, a processor that can effectively lower noise is not configured therein; hence, the measurement results may be affected due to too much noise in the process of the signal being amplified or converted. Furthermore, some conventional nano-plasmonic biosensing methods to observe the change of extinction or scattering of light by a noble metal nanostructure are usually performed by directly projecting an incident light from a light source to a sensing area. However, the lack of stable light-source control may result in an unstable incident wave of light which further affects the sensing results.

Accordingly, the inventor of the present invention has designed an optical nano-biosensing system in an effort to overcome deficiencies in terms of current techniques so as to enhance the implementation and application in industries.

SUMMARY OF THE INVENTION

In view of the aforementioned problems, the present invention provides an optical nano-biosensing system, including a nano-plasmonic sensing device, a high-resolution analog-to-digital converter, a signal acquisition and processing device, and an intelligent electronic device; wherein the nano-plasmonic sensing device further includes a light-source control circuit, a sample receiver, a light detector, and a signal-amplifying circuit. The sample receiver is connected to the light-source control circuit and receives a sample, and the light-source control circuit generates an incident light from the light source to be projected to the sample receiver. The incident light is frequency modulated at a specific modulation rate. Preferably, the light source emits a monochromatic light at a specific wavelength or a narrow-band light at a specific wavelength range. The light detector detects an emergent light from the sample receiver to generate a detection signal. The emergent light may be a transmitted light, a reflected light, or a diffracted light. The signal-amplifying circuit is connected to the light detector and converts a specific modulation frequency range of the detection signal to generate an amplified signal. The high-resolution analog-to-digital converter is connected to the signal-amplifying circuit and digitizes the amplified signal to generate a digital signal. The signal acquisition and processing device is connected to the high-resolution analog-to-digital converter and includes a signal calculator, and the signal calculator operates the digital signal to generate calculated information. The intelligent electronic device is connected to the signal acquisition and processing device and receives the calculated information, the intelligent electronic device converts the calculated information to generate sensing output information, and the sensing output information is presented on the intelligent electronic device in words, patterns, or a combination thereof.

Preferably, the light-source control circuit further includes a control circuit and a light-source projector, the control circuit correspondingly generates a light-source driving signal which is then transmitted to the light-source projector according to a feature of the light-source projector, and the light-source projector projects the incident light from the light source having a corresponding wavelength range to the sample receiver according to the light-source driving signal.

In case the signal acquisition and processing device may only process signals with non-negative voltages, a voltage-boosting circuit following the signal-amplifying circuit may further boost the amplified signal to above 0V, and the amplified signal after voltage-boosting is a non-negative value.

Preferably, the sample receiver includes a nano-plasmonic sensor and a sample vessel; the nano-plasmonic sensor is disposed in the sample vessel; the sample vessel receives and holds the sample for subsequent detection, it may be part of a microfluidic chip; the nano-plasmonic sensor includes a substrate, a plurality of noble metal nanoparticles, and a plurality of recognition molecules; the plurality of noble metal nanoparticles are disposed on the substrate; one end of each of the recognition molecules is correspondingly disposed on each of the noble metal nanoparticles; the sample vessel accommodates the sample so that the sample is in contact with the nano-plasmonic sensor; a plurality of analyte molecules in the sample bind correspondingly with the other end of each of the recognition molecules; when the nano-plasmonic sensor receives the incident light from the light source, the incident light is absorbed or scattered by the nano-plasmonic sensor; the light detector detects the emergent light of the nano-plasmonic sensor to generate the detection signal. It should be noted that the plurality of noble metal nanoparticles can be disposed on the substrate before or after the sample is introduced into the sample holder. In case the plurality of noble metal nanoparticles are to be disposed on the substrate after the sample is introduced, the same type or a second type of recognition molecules should be disposed on the substrate before the sample is introduced. The substrate may be a slide, an optical waveguide, or a grating. Preferably, the substrate is an optical waveguide. The optical waveguide may be selected from the group consisting of a cylindrical optical waveguide such as optical fiber, a planar optical waveguide such as slab waveguide and channel waveguide, and a tubular optical waveguide. In case the substrate is a slide or the like, the incident light approaches the surface of the slide perpendicularly or at a small angle of incidence (<45°), the emergent light may be a transmitted light or a reflected light. In case the substrate is an optical waveguide, the incident light may be coupled into the optical waveguide by direct focusing, prism coupling, or grating coupling at one end of the optical waveguide, and the emergent light is a transmitted light which may be coupled out at the other end of the optical waveguide by direct transmission, prism coupling, or grating coupling, respectively. In case the substrate is a grating or a grating waveguide, the incident light approaches the surface of the slide perpendicularly or at an angle, the emergent light is a diffracted light from the same side or opposite side of the grating.

Preferably, the nano-plasmonic sensor is an optical waveguide-based nano-plasmonic sensor, and most preferably, the nano-plasmonic sensor is an optical fiber-based nano-plasmonic sensor.

Preferably, the signal calculator includes a root-mean-square processor, and the root-mean-square processor operates the digital signal to generate the calculated information according to a root-mean-square algorithm.

Preferably, the signal calculator includes an absolute-mean processor, and the absolute-mean processor operates the digital signal to generate the calculated information according to an absolute-mean algorithm.

Preferably, the optical nano-biosensing system further includes a comb filter, wherein the comb filter is connected to the high-resolution analog-to-digital converter, and the comb filter operates to modify the digital signal.

Preferably, the intelligent electronic device includes an indicator acquisition processor, the indicator acquisition processor operates the calculated information to generate a plurality of indicator messages, and the intelligent electronic device is embedded with a plurality of preset threshold values; when each of the indicator messages correspondingly is in compliance with each of the preset threshold values, the intelligent electronic device determines that the calculated information as a typical molecular binding kinetic curve.

Preferably, the indicator acquisition processor includes a descent-rate indicator-acquisition unit, a surge-component indicator-acquisition unit, and a tail-signal indicator-acquisition unit; the plurality of indicator messages include a descent-rate indicator message, a surge-component indicator message, and a tail-signal indicator message; the plurality of preset threshold values include a descent-rate preset threshold value, a surge-component preset threshold value, and a tail-signal preset threshold value; the descent-rate indicator-acquisition unit operates the calculated information to generate the descent-rate indicator message; the surge-component indicator-acquisition unit operates the calculated information to generate the surge-component indicator message; the tail-signal indicator-acquisition unit operates the calculated information to generate the tail-signal indicator message; the intelligent electronic device determines that the calculated information as the typical molecular binding kinetic curve when the descent-rate indicator message is in compliance with the descent-rate preset threshold value, the surge-component indicator message is in compliance with the surge-component preset threshold value, and the tail-signal indicator message is in compliance with tail-signal preset threshold value.

Preferably, the intelligent electronic device operates the plurality of indicator messages to generate a baseline calibration message according to a baseline algorithm, and the intelligent electronic device calibrates the sensing output information according to the baseline calibration message.

Preferably, the optical nano-biosensing system further includes a Bluetooth device, wherein the Bluetooth device is connected to the signal acquisition and processing device and the intelligent electronic device, the signal acquisition and processing device transmits the calculated information to the Bluetooth device, and the Bluetooth device transmits the calculated information to the intelligent electronic device at a remote end.

On the basis of the aforementioned purpose, the present invention further provides an optical nano-biosensing method for an optical nano-biosensing system including a nano-plasmonic sensing device, a high-resolution analog-to-digital converter, a signal acquisition and processing device, and an intelligent electronic device, wherein the nano-plasmonic sensing device further includes a light-source control circuit, a sample receiver, a light detector, and a signal-amplifying circuit; the signal acquisition and processing device further includes a signal calculator; the optical nano-biosensing method includes the following steps: receiving a sample by the sample receiver; generating an incident light from the light source to be projected to the sample receiver by the light-source control circuit; detecting an emergent light from the sample receiver to generate a detection signal by the light detector; converting a specific modulation frequency range of the detection signal to generate an amplified signal by the signal-amplifying circuit; digitizing the amplified signal to generate a digital signal by the high-resolution analog-to-digital converter; operating the digital signal to generate calculated information by the signal calculator of the signal acquisition and processing device; and receiving the calculated information by the intelligent electronic device and converting the calculated information to generate sensing output information, wherein the sensing output information is presented on the intelligent electronic device in words, patterns, or a combination thereof.

In sum, the optical nano-biosensing system and method thereof of the present invention have the following advantages:

(1) The optical nano-biosensing system of the present invention provides a sample receiver, wherein the plurality of noble metal nanoparticles are disposed on the substrate, and each of the recognition molecules is correspondingly disposed on each of the noble metal nanoparticles. The sample may be introduced to the sample vessel and in contact with the nano-plasmonic sensor so that the analyte molecules in the sample bind with each of the recognition molecules. Moreover, the incident light from the light source may be properly projected onto the nano-plasmonic sensor by the light-source control circuit, and the incident light may perform multiple total internal reflections in the nano-plasmonic sensor such that the light detector may detect the emergent light from the sample receiver to generate a detection signal. With this structural configuration, each analyte molecule may be stably bound with each of the recognition molecules. In addition, since the noble metal nanoparticles may only absorb the incident light at a specific wavelength range and the substrate may effectively guide the incident light to perform multiple total internal reflections in the nano-plasmonic sensor, the light detector may thus exhibit an improved sensitivity in the detecting process.

(2) The optical nano-biosensing system of the present invention provides a signal acquisition and processing device to operate the digital signal, wherein the signal calculator of the signal acquisition and processing device includes a root-mean-square processor and an absolute-mean processor. The root-mean-square processor operates the digital signal to generate the calculated information according to a root-mean-square algorithm, whereas the absolute-mean processor operates the digital signal to generate the calculated information according to an absolute-mean algorithm. Since noise may be generated and direct current offset may occur during the process of waveforms being sensed, amplified, and voltage boosted, the signal calculator may thus be used to effectively decrease the noise to make the calculated information more accurate during the operating process.

(3) The indicator acquisition processor of the intelligent electronic device of the optical nano-biosensing system of the present invention may include a descent-rate indicator-acquisition unit, a surge-component indicator-acquisition unit, and a tail-signal indicator-acquisition unit. Each of the indicator-acquisition units operates the calculated information to respectively generate a corresponding indicator message, and the intelligent electronic device is embedded with a descent-rate preset threshold value, a surge-component preset threshold value, and a tail-signal preset threshold value. When each of the indicator messages correspondingly is in compliance with the preset threshold value, the intelligent electronic device determines that the calculated information as a typical molecular binding kinetic curve. With this system configuration, users may recognize the typical molecular binding kinetic curve by using the intelligent electronic device to further understand whether the current system condition or reaction condition functions normally.

To make the aforementioned purposes, technical features, and gains after actual implementation more obvious and understandable, the description hereinafter shall be described in more detail with reference to preferred embodiments together with related drawings.

DESCRIPTION OF THE PREFERRED EMBODIMENTS

Figure 1:
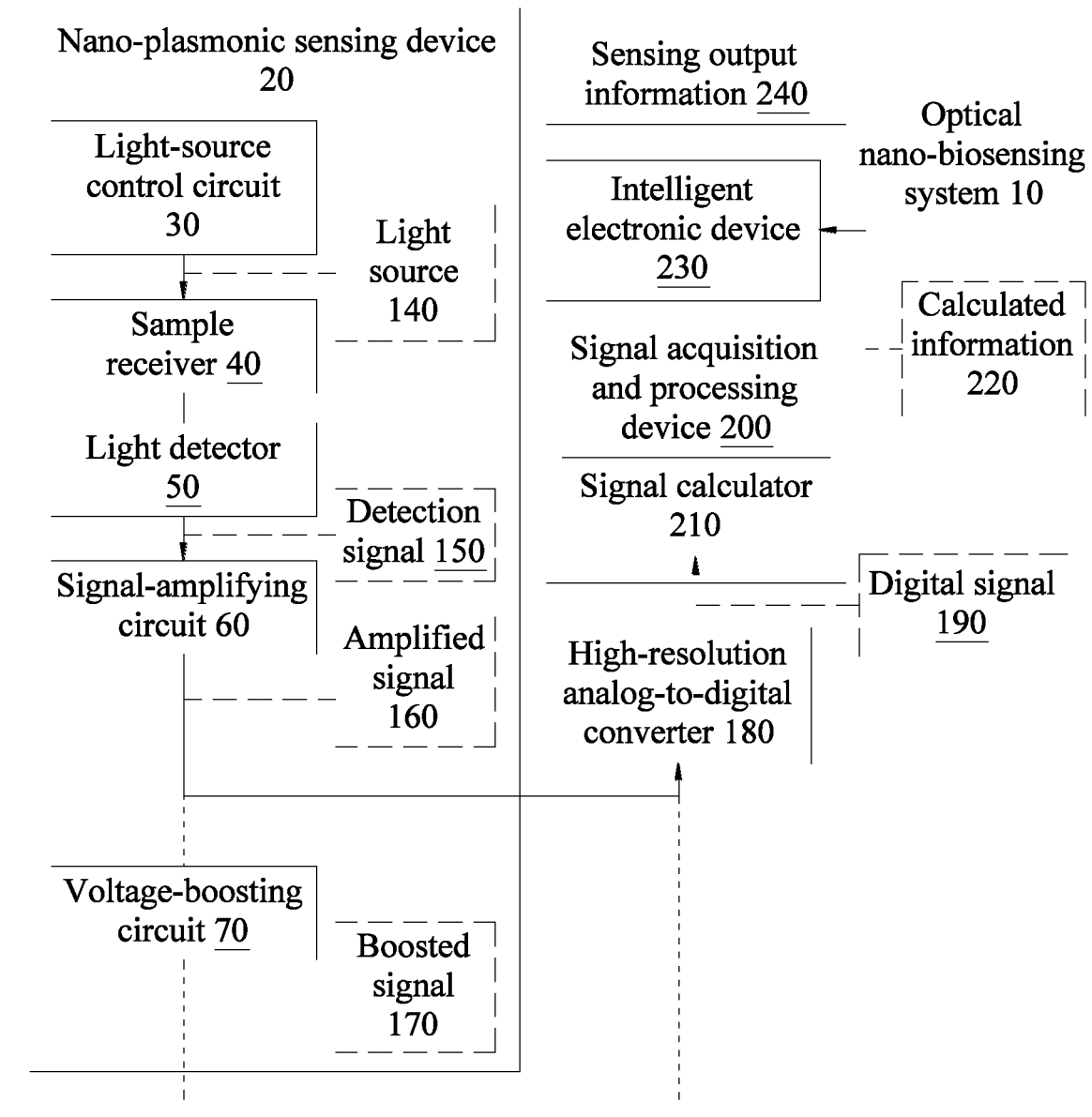
FIG. 1 depicts a system configuration diagram of the optical nano-biosensing system according to the present invention.

In the present invention, it should be noted that the orientation or positional relation regarding the terms "in," "inside," "out," and the like is based on the orientation or positional relation as shown in the drawings, which is only for ease of describing the present invention and simplifying the description. The description does not indicate or imply that the referred devices or elements must have a particular orientation, construction, and operation. Therefore, it should not be understood as a restriction on the present invention. In addition, the terms "first" and "second" are used for descriptive purposes only and are not to be construed as indicating or implying relative importance.

In the description of the present invention, it should be noted that the terms "connect", "generate", "receive", "operate", "calculate", "transmit", "dispose", "introduce", and "sense" should be considered to be general understanding unless there is a specific regulation or restriction. The specific meanings of the aforementioned terms in the present invention shall specifically be understood by a person of ordinary skill in the art.

The embodiments of the optical nano-biosensing system and method thereof of the present invention are described with reference to the related drawings. For ease of understanding, the same elements in the following embodiments are described in accordance with the same symbols.

Figure 2:
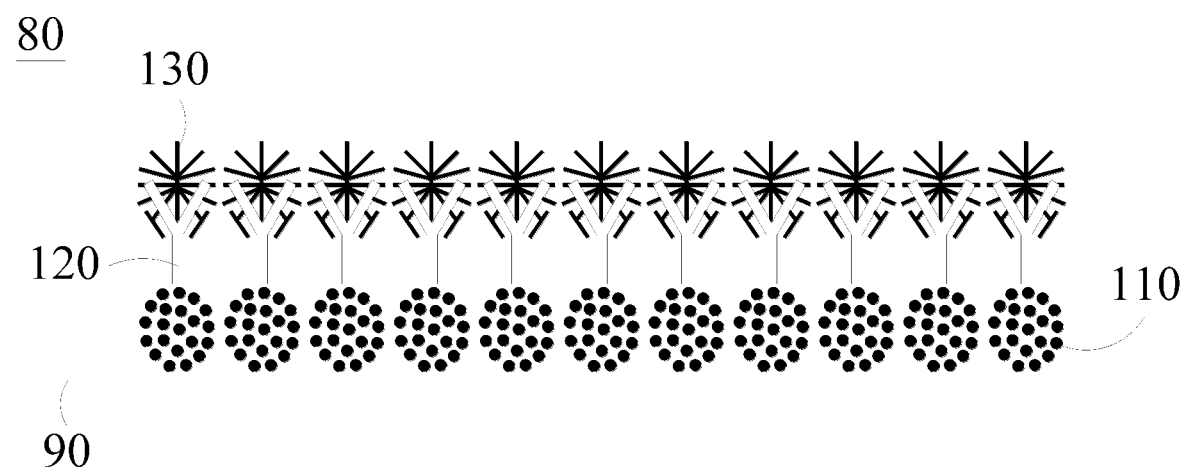
FIG. 2 depicts a schematic diagram of the nano-plasmonic sensor of the sample receiver of the optical nano-biosensing system according to the present invention.

Please refer to FIG. 1 and FIG. 2. FIG. 1 depicts a system configuration diagram of the optical nano-biosensing system according to the present invention, and FIG. 2 depicts a schematic diagram of the nano-plasmonic sensor of the sample receiver of the optical nano-biosensing system according to the present invention. As shown, the present invention provides an optical nano-biosensing system 10, including a nano-plasmonic sensing device 20, a high-resolution analog-to-digital converter 180, a signal acquisition and processing device 200, and an intelligent electronic device 230. The nano-plasmonic sensing device 20 further includes a light-source control circuit 30, a sample receiver 40, a light detector 50, and a signal-amplifying circuit 60. The sample receiver 40 is connected to the light-source control circuit 30 and receives a sample, and the light-source control circuit 30 generates an incident light from the light source 140 to be projected to the sample receiver 40. The light detector 50 detects an emergent light from the sample receiver 40 to generate a detection signal 150. The signal-amplifying circuit 60 is connected to the light detector 50 and converts a specific modulation frequency range of the detection signal 150 to generate an amplified signal 160. The high-resolution analog-to-digital converter 180 is connected to the signal-amplifying circuit 60 and digitizes the amplified signal 160 to generate a digital signal 190, wherein the high-resolution thereof is defined at 12 bits or more. The signal acquisition and processing device 200 is connected to the high-resolution analog-to-digital converter 180 and includes a signal calculator 210, and the signal calculator 210 operates the digital signal 190 to generate calculated information 220. The intelligent electronic device 230 is connected to the signal acquisition and processing device 200 and receives the calculated information 220, the intelligent electronic device 230 converts the calculated information 220 to generate sensing output information 240, and the sensing output information 240 is presented on the intelligent electronic device 230 in words, patterns, or a combination thereof.

The light-source control circuit 30 may further include a control circuit and a light-source projector. The control circuit correspondingly generates a light-source driving signal which is then transmitted to the light-source projector according to a feature of the light-source projector, and the light-source projector projects the incident light from the light source 140 having a corresponding wavelength range to the sample receiver 40 according to the light-source driving signal to make the incident light from the light source 140 perform multiple total internal reflections in the sample receiver 40. Wherein, the control circuit may automatically calibrate the intensity of the light-source driving signal according to the feature of the light-source projector to further make the incident light from the light source 140 projected from the light-source projector have corresponding light intensity. In addition, the control circuit may further simultaneously control the plurality of incident lights from the light-source projectors.

In some cases, the signal acquisition and processing device 200 may only be able to process signals with non-negative voltages; thus, the optional voltage-boosting circuit 70 may further be utilized to boost the amplified signal 160 to above 0V to generate the boosted signal 170 having a non-negative value. In this way, the follow-up digital signals generated by the high-resolution analog-to-digital converter 180 digitizing the boosted signal 170 from the amplified signal 160 are also non-negative values. Thus, the signal acquisition and processing device 200 may operate the digital signal 190 with non-negative voltages.

The sample receiver 40 may include a nano-plasmonic sensor 80 and a sample vessel. The nano-plasmonic sensor 80 is disposed in the sample vessel. The nano-plasmonic sensor 80 includes a substrate 90, a plurality of noble metal nanoparticles 110, and a plurality of recognition molecules 120; the plurality of noble metal nanoparticles 110 are disposed on the substrate 110. One end of each of the recognition molecules 120 is correspondingly disposed on each of the noble metal nanoparticles 110; the sample vessel receives the sample so that the sample is in contact with the nano-plasmonic sensor 80; a plurality of analyte molecules 130 in the samples bind correspondingly with the other end of each of the recognition molecules 120. Wherein, the substrate 90 is formed by using a $CO_2$ laser to remove the cladding of an optical fiber to form a sensing region, and a plurality of noble metal nanoparticles 110 are disposed on the sensing region. Furthermore, since the plurality of recognition molecules 120 are made of biomolecules having high selectivity, they may bind effectively with a particular plurality of analyte molecules 130 in the sample. In addition, the sample vessel may connect to a sample injector and tubing; thus, the sample may be effectively guided to flow into the nano-plasmonic sensor 80. The noble metal nanoparticles 110 may be gold nanoparticles or silver nanoparticles, and the shapes of the noble metal nanoparticles include a nanosphere, a nanorod, a nanoring, a nanoplate, a dendrimer-like, a nanocube, a nanoprism, or a nanonetwork, and the like. Wherein, the recognition molecules 120 may be antibodies, peptides, hormone receptors, lectins, carbohydrates, chemical recognition molecules, deoxyribonucleic acid, ribonucleic acid, nucleic acid aptamers, and the like.

The nano-plasmonic sensor 80 may include the substrate modified by the noble metal nanoparticles. The incident light from the light source is projected onto the noble metal nanoparticles on the substrate perpendicularly or at an angle and it may be absorbed or scattered, and the variation in the intensity of the emergent light transmitted or reflected may be used to calculate the amount of analyte. In addition, the nano-plasmonic sensor 80 may be an optical waveguide-based nano-plasmonic sensor or an optical fiber-based nano-plasmonic sensor, wherein the type of optical waveguide may include cylindrical optical waveguide, slab waveguide, channel waveguide, and tubular optical waveguide, whereas the optical fiber type be a particular type of cylindrical optical waveguide. The noble metal nanoparticles modified on the surface of the optical waveguide or the unclad surface of the optical fiber. When the optical waveguide-based nano-plasmonic sensor or the optical fiber-based nano-plasmonic sensor receives the incident light from the light source, the incident light from the light source is at one end of the optical waveguide or optical fiber and performs multiple total internal reflections in the optical waveguide or optical fiber. When measuring the emergent light at the other end of the optical waveguide or optical fiber, the sensitivity of the nano-plasmonic sensing may be greatly increased. Furthermore, the amount of variation in evanescent-wave intensity may be greatly increased through multiple total internal reflections, thus greatly increasing the sensitivity of the nano-plasmonic sensing.

When the nano-plasmonic sensor 80 receives the incident light from the light source 140, the incident light from the light source 140 performs multiple total internal reflections in the nano-plasmonic sensor 80, and the light detector 50 detects the emergent light from the nano-plasmonic sensor 80 to generate the detection signal 150. With this structural configuration, the incident light from the light source 140 may be stably guided in the nano-plasmonic sensor 80 through the substrate 90 via multiple total internal reflections, and since the plurality of noble metal nanoparticles 110 may only absorb or scatter the incident light from the light source 140 at a specific wavelength, the light detector 50 may thus exhibit a higher sensitivity during the sensing process.

The optical nano-biosensing system 10 may further include a Bluetooth device. The Bluetooth device is connected to the signal acquisition and processing device 200 and the intelligent electronic device 230, the signal acquisition and processing device 200 transmits the calculated information 220 to the Bluetooth device, and the Bluetooth device transmits the calculated information 220 to the intelligent electronic device 230 at a remote end.

The signal calculator 210 includes a root-mean-square processor, and the root-mean-square processor operates the digital signal 190 to generate the calculated information 220 according to a root-mean-square (RMS) algorithm.

The signal calculator includes an absolute-mean processor, and the absolute-mean processor operates the digital signal 190 to generate the calculated information 220 according to an absolute-mean algorithm.

The optical nano-biosensing system 10 further includes a comb filter, wherein the comb filter is connected to the high-resolution analog-to-digital converter 180, and the comb filter operates to modify the digital signal 190.

Figure 3A:
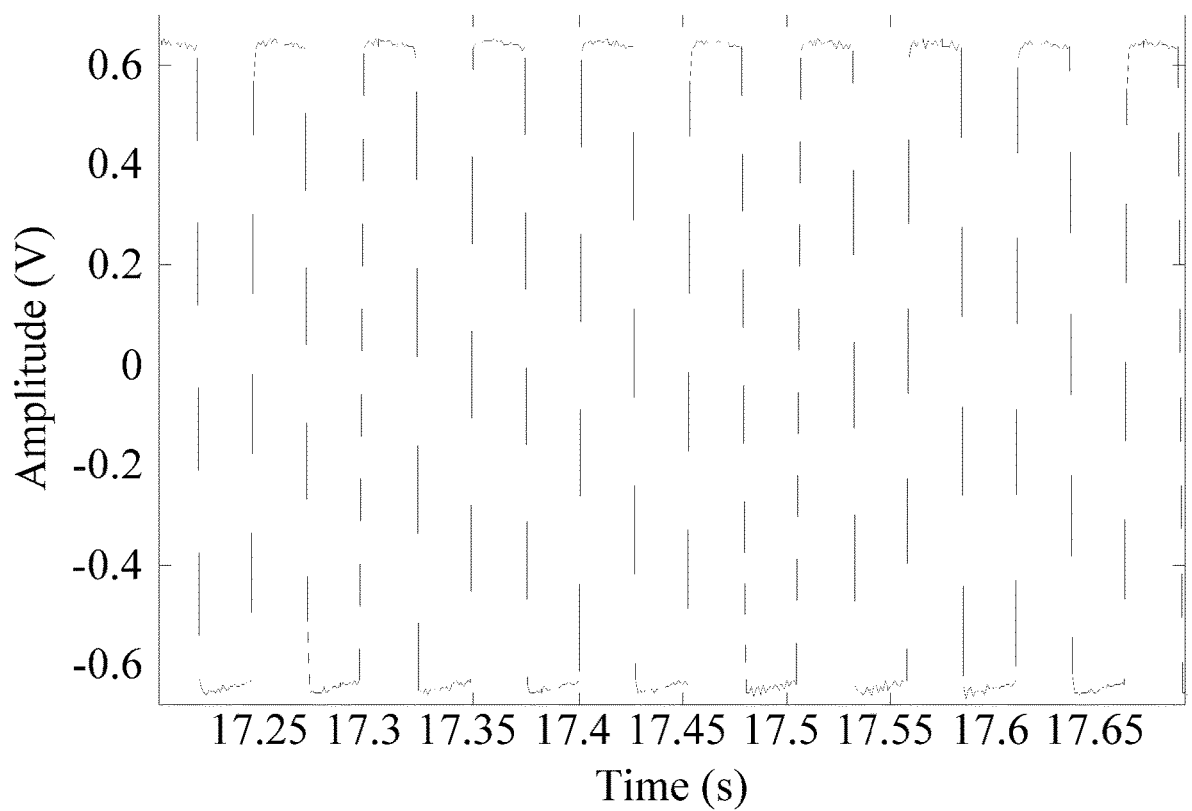
FIG. 3a depicts the first waveform schematic diagram of the root-mean-square processor of the optical nano-biosensing system according to the present invention.
Figure 3B:
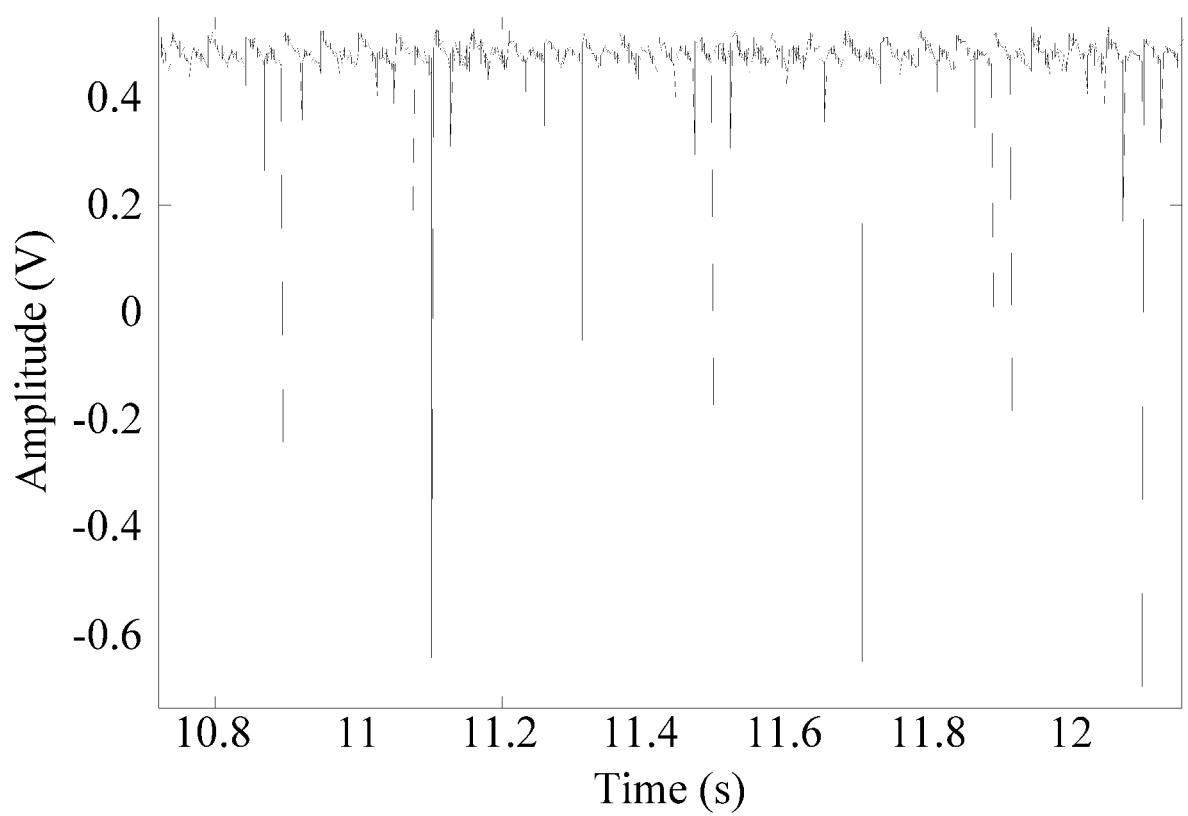
FIG. 3b depicts the second waveform schematic diagram of the root-mean-square processor of the optical nano-biosensing system according to the present invention.

Please refer to FIG. 3a and FIG. 3b. FIG. 3a depicts the first waveform schematic diagram of the root-mean-square processor of the optical nano-biosensing system according to the present invention. FIG. 3b depicts the second waveform schematic diagram of the root-mean-square processor of the optical nano-biosensing system according to the present invention. As shown, the signal calculator 210 includes the root-mean-square processor. The root-mean-square processor operates the digital signal 190 to generate the calculated information 220 according to the root-mean-square algorithm, wherein the root-mean-square algorithm is based on the concept of being averaged, which may be used to observe the stable state of the signal received per second. Since the voltage-boosting circuit 70 may boost the amplified signal 160 to above 0V, the average value is subtracted from the voltage thereof in the root-mean-square algorithm so that the first waveform with symmetry in positive and negative values may be obtained. The second waveform may be obtained after taking an absolute value. This waveform contains noise and the intensity thereof is a half of that of the amount of variation in the original waveform. Hence, the present invention re-designs the algorithm, wherein $x_i$ is the signal voltage, $\bar{x}$ is the average value of the signal voltage, and the derivation may be shown in Equation (1) to (6):

$$\sqrt{\frac{1}{N}\sum_{i=1}^{N}(x_i - \bar{x})^2} = \sqrt{\frac{1}{N}\sum_{i=1}^{N}(x_i^2 - 2x_i\bar{x} + \bar{x}^2)}, \bar{x} = \frac{1}{N}\sum_{i=1}^{N} x_i \quad (1)$$

$$= \sqrt{\frac{1}{N}\left[\sum_{i=1}^{N} x_i^2 - \frac{2}{N}\sum_{i=1}^{N} x_i \sum_{i=1}^{N} x_i + N\left(\frac{1}{N}\sum_{i=1}^{N} x_i\right)^2\right]} \quad (2)$$

$$= \sqrt{\frac{1}{N}\left[\sum_{i=1}^{N} x_i^2 - \frac{2}{N}\left(\sum_{i=1}^{N} x_i\right)^2 + \frac{1}{N}\left(\sum_{i=1}^{N} x_i\right)^2\right]} \quad (3)$$

$$= \sqrt{\frac{1}{N}\left[\sum_{i=1}^{N} x_i^2 - \frac{1}{N}\left(\sum_{i=1}^{N} x_i\right)^2\right]} \quad (4)$$

$$= \sqrt{\frac{1}{N}\sum_{i=1}^{N} x_i^2 - \left(\sum_{i=1}^{N} x_i\right)^2} \quad (5)$$

$$= \sqrt{\frac{1}{N}\sum_{i=1}^{N} x_i^2 - \bar{x}^2} \quad (6)$$

Wherein, when calculating the value of $\bar{x}$, it is only needed to calculate the accumulated value of $x_i$, and then make an average. Neither the value nor the square value thereof is not big enough, but they may exceed the maximum value the register of the root-mean-square processor can tolerate when calculating the accumulated value of $x_i^2$. Thus, in the root-mean-square processor, the present invention adopts two registers, A0 and A1, to store the value accumulated by $x_i^2$. After every accumulation, the first register A0 is compared to the previous value. Being smaller than the previous value indicates the occurrence of overflow. In the meantime, the second register A1 is added with 1, and when the accumulated value of $x_i^2$ needs to be averaged, the value may be (2M×A1+A0)/N when taking the register with M bits for example. However, to avoid the occurrence of an overflow in the calculating process, 2M is divided by 2 and then averaged. Then, this value is multiplied by the value of the second register A1 and then multiplied again by 2. Finally, the obtained value is added with the value of the first register A0 being averaged. For example, the result of a register with 32 bits is (231÷N×A1×2)+(A0÷N). This method may be used to solve the problem of a register having an overflow in the calculating process.

Figure 4:
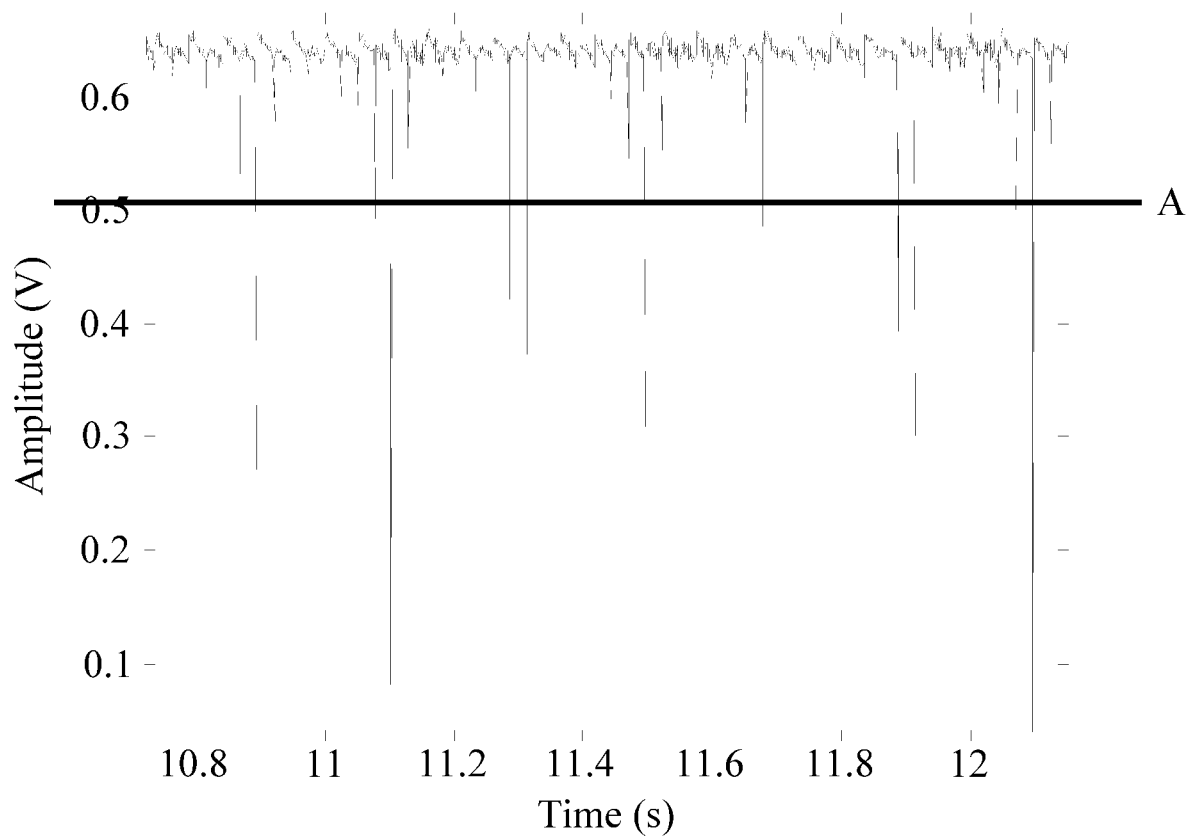
FIG. 4 depicts a waveform schematic diagram of the absolute-mean processor added with a threshold value of the optical nano-biosensing system according to the present invention.

Please refer to FIG. 4 which depicts a waveform schematic diagram of the absolute-mean processor added with a threshold value of the optical nano-biosensing system according to the present invention. The signal calculator includes an absolute-mean processor, and the absolute-mean processor operates the digital signal 190 to generate the calculated information 220 according to an absolute-mean algorithm. In the absolute-mean processor, the overall average value of the digital signal 190 is calculated. Every point of the signal is subtracted by the average value and then taken an absolute value. The waveform contains noise and the intensity is half of the amount of variation of the original waveform. Finally, the values in total are added up and averaged. The purpose thereof is similar to that of the root-mean-square algorithm. The noise in the signal is eliminated by the method of average. The result is positively proportional to half of the intensity of the mean-square wave after the noise elimination. As shown in Equation (7), $x_i$ is the signal voltage, and x is the average value of the signal voltage.

$$\frac{1}{n}\sum_{i=1}^{n}(|x_i - \bar{x}|), \bar{x} = \frac{1}{n}\sum_{i=1}^{n} x_i \quad (7)$$

In addition, the variation of the nano-plasmonic resonance of the noble metal nanoparticles 110 occurs at the positions of the crest and trough of the wave. Therefore, after the digital signal 190 is taken an absolute value and becomes positive, the present invention may be added with a threshold value. The added threshold value is shown in FIG. 4 and marked as line A. The obvious noise below the threshold value is eliminated, and the variation of the intensity which is more correct is then calculated.

The present invention evaluates the trend of the signal after each processor of the signal calculator 210 is operated by the relative standard deviation (RSD), which is indicated in percentage. The calculation of RSD is presented in Equation (8), wherein SD is the standard deviation of the signal and $\bar{X}$ is the average value of the signal. Each calculation is made based on the received data 200 seconds ago to evaluate the current status of the signal.

$$RSD = \frac{SD}{\bar{X}} \times 100\% \quad (8)$$

Wherein, the greater the RSD, the more scattered the data. In other words, the greater the RSD, the larger change of the signal in the time chain. When the nano-plasmonic sensing device 20 functions, the local refractive index at the noble metal particle surface in the sample receiver 40 changes when molecular binding occur between the recognition molecules and the analyte molecules, resulting in changes in the intensity of the emergent light from the nano-plasmonic sensing device 20. Then a plot of the signal versus time during the molecular binding process leads to a molecular binding kinetic curve. Therefore, the variation of the molecular binding kinetic signal in the initial phase after being operated by the follow-up processors and devices is greater, meaning that the value of the RSD is greater. After the molecular binding reaction reaches equilibrium, the variation of the molecular binding kinetic signal largely reduces, making the value of the RSD being relatively small. For the present invention, an RSD threshold value (for instance, 0.015%) of the signal is regarded as a cutoff value for the determination of the reaction status. The RSD value of the signal below the threshold value means that the molecular binding reaction in the molecular binding kinetic curve reaches a steady state. In other words, the molecular binding reaction reaches equilibrium in this time frame. The allows one to stop the data acquisition to save time because the reaction is almost completed.

In the evaluation process of the RSD, the sample receiver 40 may take de-ionized water as a sample and imports it herein. The signal acquisition and processing device operates the digital signal 190 to generate the calculated information 220. Then, analyzed by the Matlab program together with the setting of three times of the RSD as the noise level, the result is presented as in Table 1. In Table 1, it may be seen that the effect of the root-mean-square processor is slightly better than that of the absolute-mean processor with a threshold value, and the effect of the absolute-mean processor with a threshold value is also better than that of the absolute-mean processor without a threshold value.

TABLE 1

Comparison of the stability of each processor of the signal calculator

|  | Root-mean-square processor | Absolute-mean processor | Absolute-mean processor added with a threshold value (Threshold value = 0.7) |
|---|---|---|---|
| RSD1 | 0.0032% | 0.0040% | 0.0033% |
| RSD2 | 0.0023% | 0.0029% | 0.0023% |
| RSD3 | 0.0019% | 0.0028% | 0.0021% |

Figure 5A:
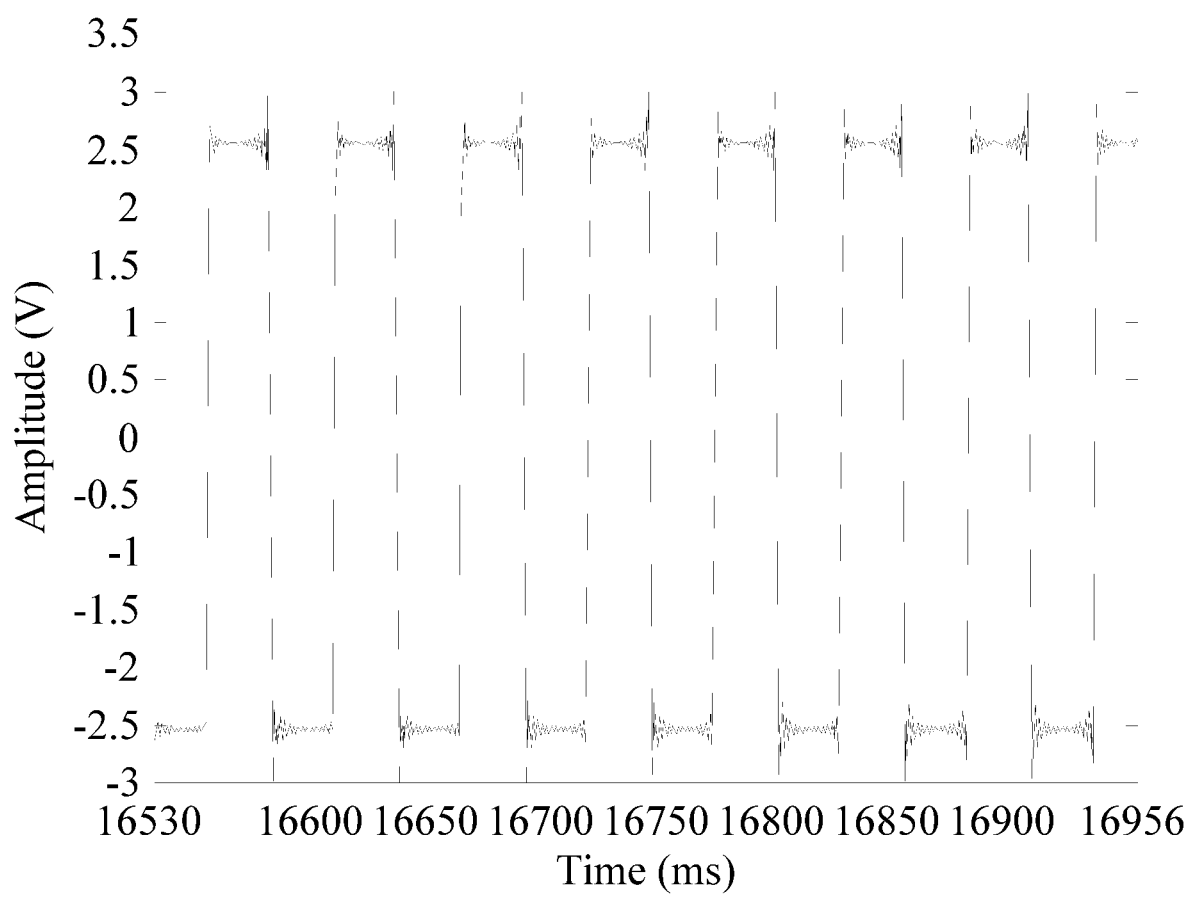
FIG. 5a depicts a square-wave schematic diagram corresponding to the original digital signal of the optical nano-biosensing system according to the present invention.
Figure 5B:
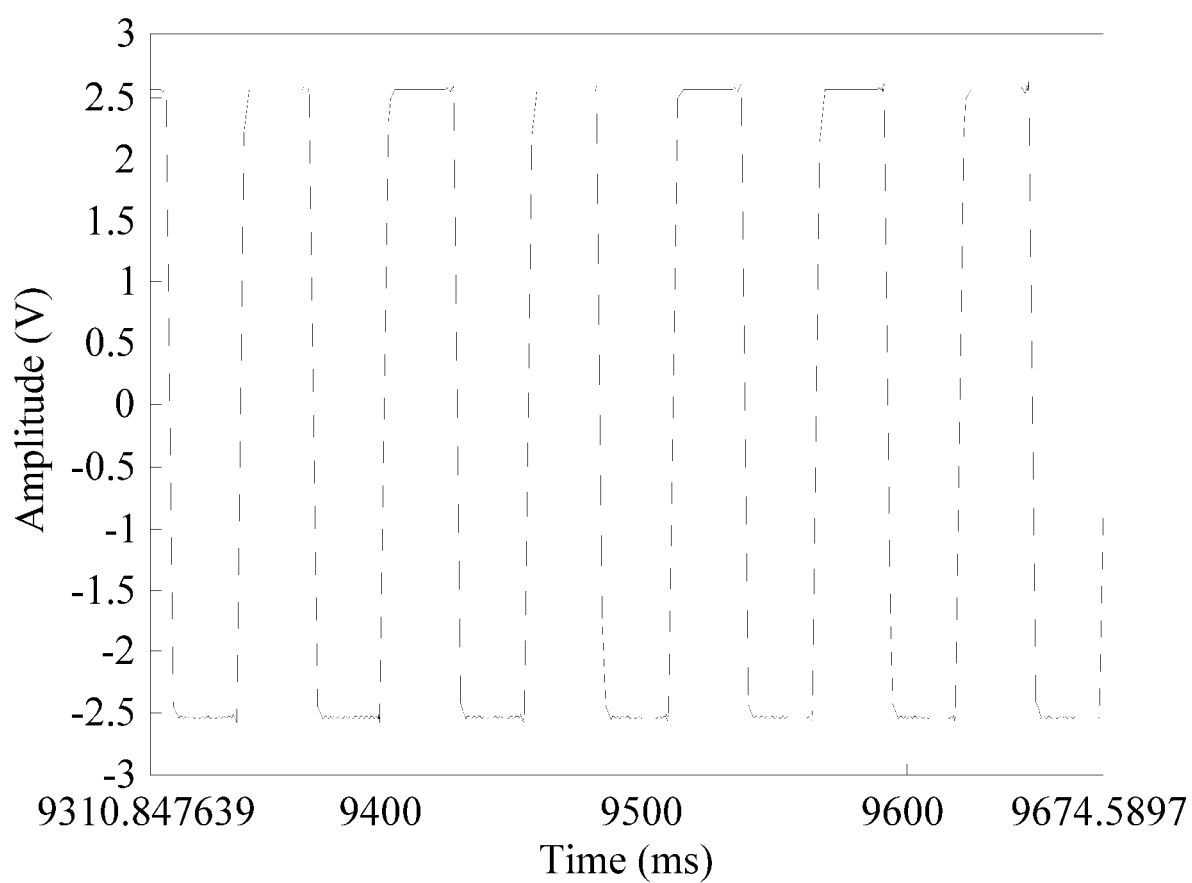
FIG. 5b depicts a square-wave schematic diagram corresponding to the digital signal operated by the comb filter of the optical nano-biosensing system according to the present invention.

Please refer to FIG. 5a and FIG. 5b. FIG. 5a depicts a square-wave schematic diagram corresponding to the original digital signal of the optical nano-biosensing system. FIG. 5b depicts a square-wave schematic diagram corresponding to the digital signal operated by the comb filter of the optical nano-biosensing system. As shown, after the incident light from the light source 140 undergoes multiple total internal reflections in the nano-plasmonic sensor 80, the light detector 50 detects the emergent light and generates a detection signal 150, the signal-amplifying circuit 60 converts the detection signal 150 to generate an amplified signal 160. Furthermore, the high-resolution analog-to-digital converter 180 digitizes the amplified signal 160 to generate 190. Through the above conversion process, the waveform corresponding to the digital signal 190 is a square wave with noise and ripples. Therefore, the present invention uses the comb filter to operate the digital signal 190 to lower the noise and ripples of the square wave corresponding to the digital signal 190, thus decreasing the noise and improving the quality of the digital signal 190.

The present invention further conducts a test on the result of the comb filter. The test method is to use a waveform with 1 KHz to excite the light-source control circuit 30 to generate a corresponding incident light from the light source 140 to be projected onto the nano-plasmonic sensor, and also use a 24-bit signal acquisition device to respectively perform sampling on the original digital signal 190 and the digital signal 190 operated by the comb filter by 50 kHz in order to determine the difference between the square waves corresponding to the two, wherein the processor used in the signal acquisition device is NI-9234. It may be known from FIG. 5a that the square wave generated after the digital signal 190, not operated by the comb filter, is sampled by the digital acquisition device may obviously have the noise and ripples. As for FIG. 5b, it may be confirmed that the noise and ripples of the square wave generated after the digital signal 190, operated by the comb filter, is sampled by the digital acquisition device obviously decrease.

Figure 6:
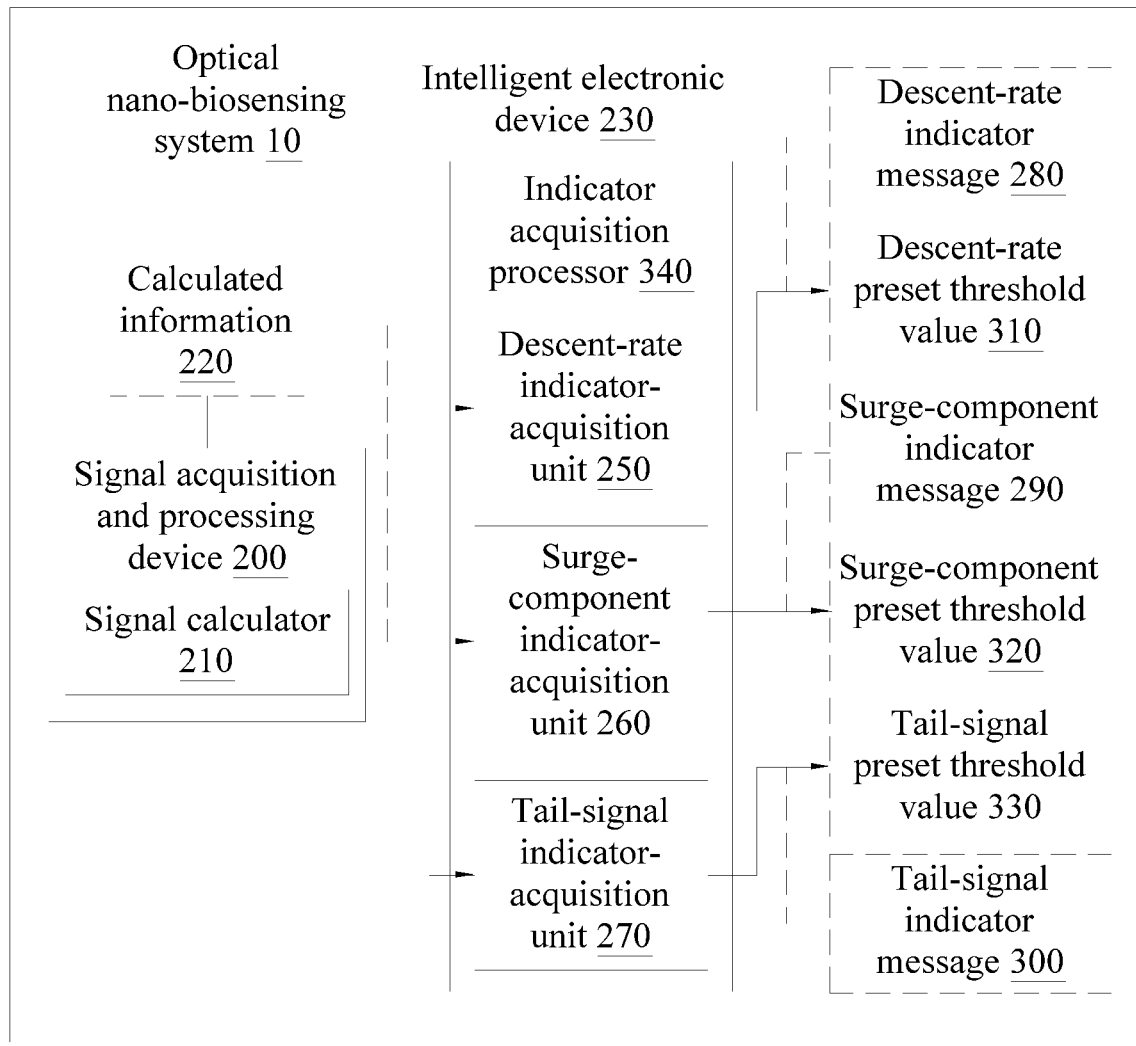
FIG. 6 depicts a configuration diagram of the intelligent electronic device determining a typical molecular binding kinetic curve of the optical nano-biosensing system according to the present invention.

Please refer to FIG. 6 which depicts a configuration diagram of the intelligent electronic device determining a typical molecular binding kinetic curve of the optical nano-biosensing system according to the present invention. As shown, the intelligent electronic device includes an indicator acquisition processor, the indicator acquisition processor operates the calculated information to generate a plurality of indicator messages, and the intelligent electronic device is embedded with a plurality of preset threshold values; when each of the indicator messages correspondingly is in compliance with each of the preset threshold values, the intelligent electronic device determines that the calculated information as a typical molecular binding kinetic curve.

Wherein, the indicator acquisition processor further includes a descent-rate indicator-acquisition unit 250, a surge-component indicator-acquisition unit 260, and a tail-signal indicator-acquisition unit 270. The plurality of indicator messages include a descent-rate indicator message 280, a surge-component indicator message 290, and a tail-signal indicator message 300. The plurality of preset threshold values includes a descent-rate preset threshold value 310, a surge-component preset threshold value 320, and a tail-signal preset threshold value 330. The descent-rate indicator-acquisition unit 250 operates the calculated information 220 to generate the descent-rate indicator message 280. The surge-component indicator-acquisition unit 260 operates the calculated information 220 to generate the surge-component indicator message 290. The tail-signal indicator-acquisition unit 270 operates the calculated information 220 to generate the tail-signal indicator message 300. The intelligent electronic device 230 determines that the calculated information 220 as the typical molecular binding kinetic curve when the descent-rate indicator message 280 is in compliance with the descent-rate preset threshold value 310, the surge-component indicator message 290 is in compliance with the surge-component preset threshold value 320, and the tail-signal indicator message 300 is in compliance with tail-signal preset threshold value 330. To reduce the computational complexity and quickly analyze the molecular binding kinetic curve, only the decline rate of the reaction point, the surge component, and the tail signal of the calculated information 220 are used for determining whether the molecular binding kinetic curve is typical. When the indicator messages generated corresponding to the calculated information 220 operated by each indicator unit are in compliance with the corresponding threshold value embedded in the intelligent electronic device 230, the intelligent electronic device 230 determines that the calculated information as a typical molecular binding kinetic curve.

The descent-rate indicator-acquisition unit 250 operates the calculated information 220 to generate the descent-rate indicator message 280. It may be observed that although the typical molecular binding kinetic curve drops rapidly in the initial phase of the reaction, this curve descends in a curved line in the middle phase of the reaction. In contrast, the non-typical molecular binding kinetic curve very often descends perpendicularly. The descent rate of signal over the reaction points at the moment would be extremely large. Hence, calculating the descent rate of signal from one reaction point to the next reaction point at any moment in the range of the reaction curve may be regarded as a reference designator for identifying whether it is a typical molecular binding kinetic curve, wherein the operational method of the descent-rate indicator-acquisition unit 250 is shown as in Equation (9), where $X_{drop}$ refers to the signal intensity at one reaction point; $X_{drop+1}$ refers to the intensity at the next reaction point; $X_{max}$ refers to the maximum signal intensity; $X_{min}$ refers to the minimum signal intensity.

$$\frac{X_{drop} - X_{drop+1}}{X_{max} - X_{min}} \times 100\% \quad (9)$$

The surge-component indicator-acquisition unit 260 operates the calculated information 220 to generate the surge-component indicator message 290, wherein the reason for the non-typical molecular binding kinetic curve is often due to external factors to allow the occurrence of the surge, making the noise of the signal too large in the experiment. Therefore, the mechanism of surge determination is added herein, and the operational method of the surge-component indicator-acquisition unit 260 is used to search for the percentage of the maximum of n surges in the range of the molecular binding kinetic curve, as shown in Equation (10), where $X_{surge}$ refers to the magnitude of a surge.

$$\frac{\text{Max}\{X_{surge1}, X_{surge2}, \ldots, X_{surgen}\}}{X_{max} - X_{min}} \times 100\% \quad (10)$$

The tail-signal indicator-acquisition unit 270 operates the calculated information 220 to generate the tail-signal indicator message 300. Regarding identifying the typical or non-typical molecular binding kinetic curve, the signal variation at the completion of the reaction is also one of the important indicators. One-fifth of the overall interval at the final phase of the molecular binding kinetic curve is taken as a determination interval. The operational method of the tail-signal indicator-acquisition unit 270 is as shown in Equation (11), where $X_{end\_max}$ refers to the maximum of the tail signal, and $X_{end\_min}$ refers to the minimum of the tail signal:

$$\frac{X_{end\_max} - X_{end\_min}}{X_{max} - X_{min}} \times 100\% \quad (11)$$

Figure 7A:
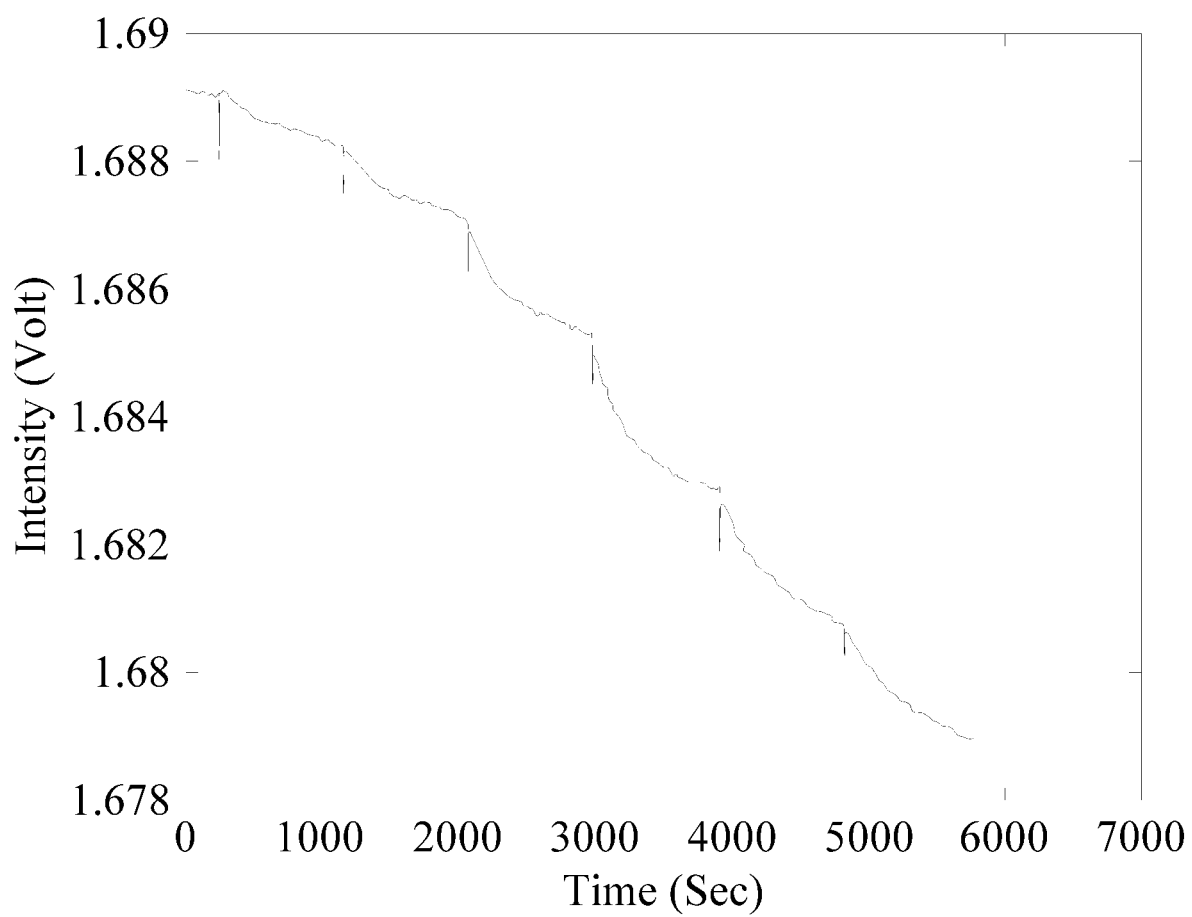
FIG. 7a depicts a schematic diagram of the original reaction curve of the sensing output information of the optical nano-biosensing system according to the present invention.
Figure 7B:
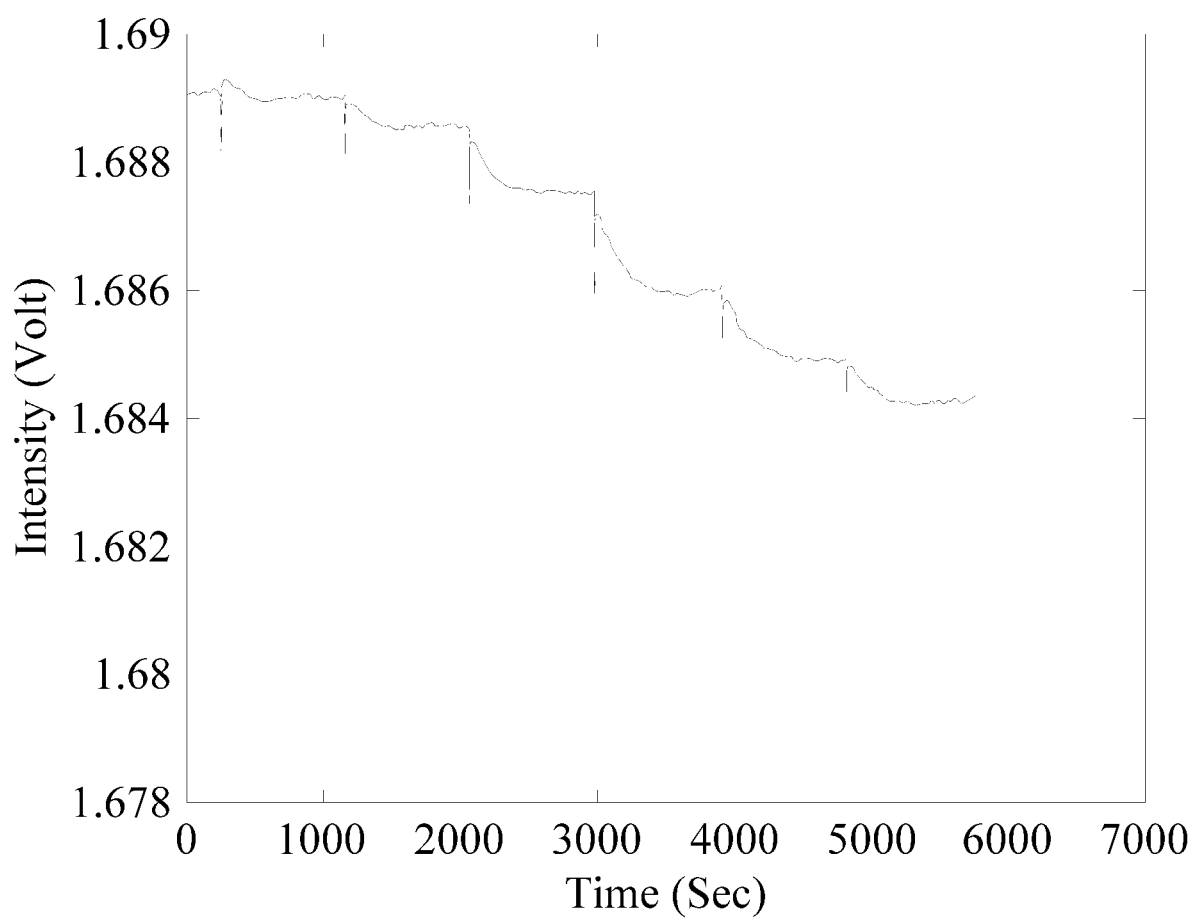
FIG. 7b depicts a schematic diagram of the reaction curve of the sensing output information calibrated by the baseline calibration message of the optical nano-biosensing system according to the present invention.

Please refer to FIGS. 7a and 7b. FIG. 7a depicts a schematic diagram of the original molecular binding reaction curve of the sensing output information of the optical nano-biosensing system according to the present invention. FIG. 7b depicts a schematic diagram of the molecular binding reaction curve of the sensing output information calibrated by the baseline calibration message of the optical nano-biosensing system according to the present invention. As shown, the intelligent electronic device 230 operates a plurality of indicator messages to generate a baseline calibration message according to a baseline algorithm. The intelligent electronic device 230 calibrates the sensing output information 240 according to the baseline calibration message. The baseline of the molecular binding reaction curve in the sensing output information 240 may decline continuously with a slow trend because of the feature of photoelectric systems. In an experiment with injection of multiple samples of increasing analyte concentration, the trends of the residual signals from the previous sample injections are often added to the signal of the current sample injection in addition to the slow baseline drift trend. Hence, the present invention utilizes the intelligent electronic device 230 to operate a plurality of indicator messages according to a baseline algorithm to generate a baseline calibration message. This baseline calibration message contains the baseline draft trend and the trends of the residual signals from the previous sample injections. Furthermore, the baseline calibration message calibrates the sensing output information 240 to allow the latter segment of each sample injection in the molecular binding reaction curve of the sensing output information 240 shown on the intelligent electronic device 230 to present an extremely flat variation. Therefore, the completion of each molecular binding reaction for each sample injection may be accurately displayed so as to show the state of reaction equilibrium.

Figure 8:
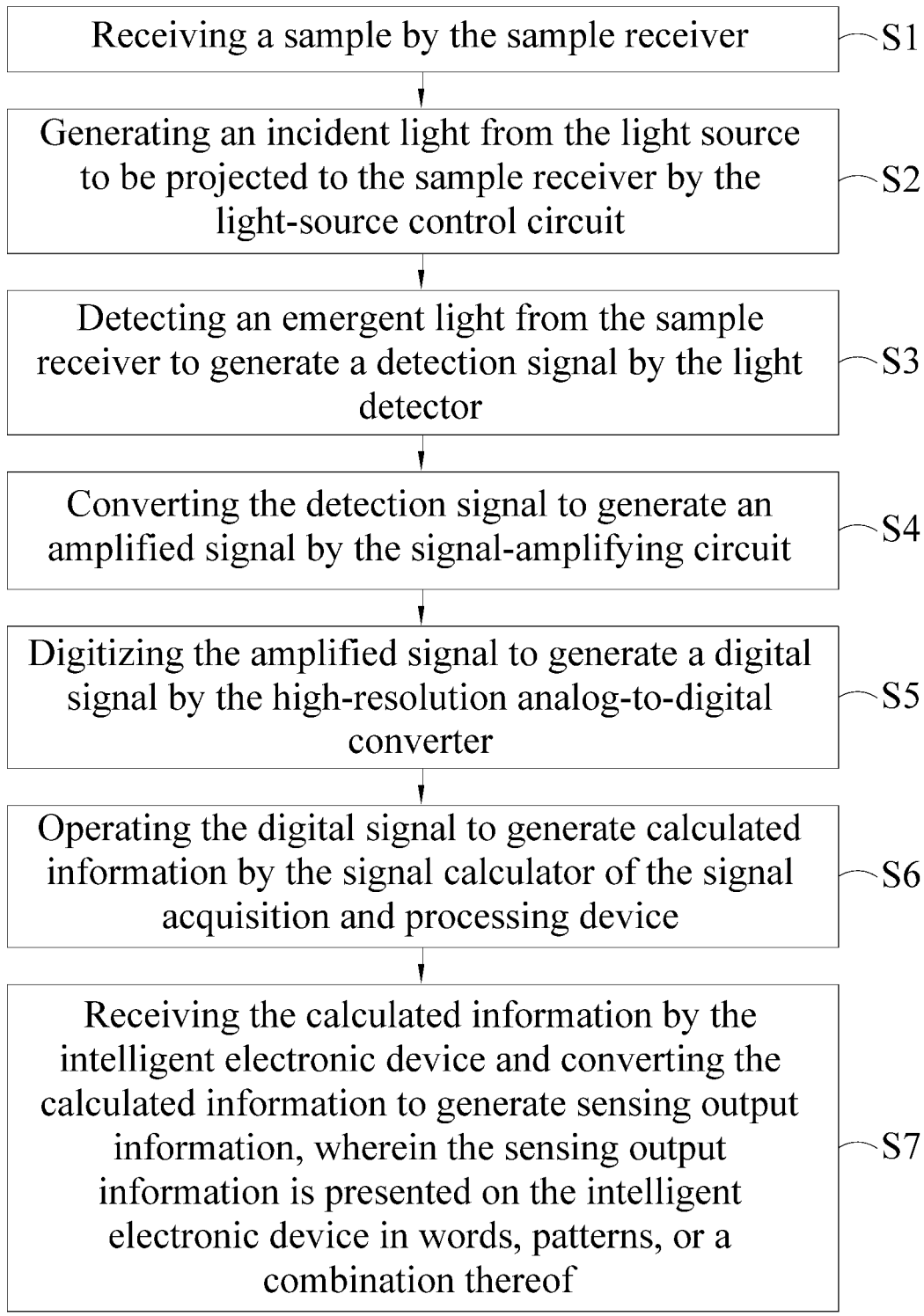
FIG. 8 depicts a flowchart of the optical nano-biosensing method according to the present invention.

Please refer to FIG. 8 which depicts a flowchart of the optical nano-biosensing method according to the present invention. As shown, the present invention further provides an optical nano-biosensing method for an optical nano-biosensing system 10 including a nano-plasmonic sensing device 20, a high-resolution analog-to-digital converter 180, a signal acquisition and processing device 200, and an intelligent electronic device 230. The nano-plasmonic sensing device further includes a light-source control circuit 30, a sample receiver 40, a light detector 50, and a signal-amplifying circuit 60; the signal acquisition and processing device 200 further includes a signal calculator 210; the optical nano-biosensing method includes the following steps:

Step S1: receiving a sample by the sample receiver;

Step S2: generating an incident light from the light source 140 to be projected to the sample receiver 40 by the light-source control circuit 30;

Step S3: detecting an emergent light from the sample receiver 40 to generate a detection signal 150 by the light detector 50;

Step S4: converting the detection signal 150 to generate an amplified signal 160 by the signal-amplifying circuit 60;

Step S5: digitizing the amplified signal 160 to generate a digital signal 190 by the high-resolution analog-to-digital converter 180;

Step S6: operating the digital signal 190 to generate calculated information 220 by the signal calculator 210 of the signal acquisition and processing device 200;

Step S7: receiving the calculated information 220 by the intelligent electronic device 230 and converting the calculated information 220 to generate sensing output information 240, wherein the sensing output information 240 is presented on the intelligent electronic device 230 in words, patterns, or a combination thereof. The sample may be introduced to the sample vessel and in contact with the nano-plasmonic sensor so that the analyte molecules in the sample bind with each of the recognition molecules.

Compared to the conventional biosensing method, the optical nano-biosensing system and method thereof of the present invention 10 provides a sample receiver 40, wherein the plurality of noble metal nanoparticles 110 are disposed on the substrate 90, and each of the recognition molecules 120 is correspondingly disposed on each of the noble metal nanoparticles 110. The sample may be introduced to the sample vessel and in contact with the nano-plasmonic sensor 80 so that the analyte molecules 130 in the sample bind with each of the recognition molecules 120. Moreover, the incident light from the light source 140 may be properly projected onto the nano-plasmonic sensor 80 by the light-source control circuit 30, and the incident light from the light source 140 may be absorbed or scattered by the nano-plasmonic sensor 80. At the moment, the detection signal 150 may be generated by detecting the emergent light from the sample receiver 40 by the light detector 50. With this structural configuration, each analyte molecule 130 may bind with each of the recognition molecules 120. In addition, since the noble metal nanoparticles 110 may only absorb or scatter the incident light from the light source 140 at a specific wavelength range and if the substrate 90 is an optical waveguide-based nano-plasmonic sensor or an optical fiber-based nano-plasmonic sensor, the incident light from the light source 140 may thus be effectively guided to perform multiple total internal reflections in the nano-plasmonic sensor 80 so that the light detector 50 may exhibit a higher sensitivity during the sensing process.

The optical nano-biosensing system 10 of the present invention further provides a signal acquisition and processing device 200 to operate the digital signal 190, wherein the signal calculator 210 of the signal acquisition and processing device 200 includes a root-mean-square processor and an absolute-mean processor. The root-mean-square processor operates the digital signal 190 to generate the calculated information 220 according to a root-mean-square algorithm, whereas the absolute-mean processor operates the digital signal 190 to generate the calculated information 220 according to an absolute-mean algorithm. Since noise may be generated and direct current offset may occur during the process of waveforms being sensed, amplified, and voltage boosted, the signal calculator 210 may thus be used to effectively decrease the noise to make the calculated information 220 more accurate during the operating process.

The indicator acquisition processor of the intelligent electronic device 230 of the optical nano-biosensing system 10 of the present invention may include a descent-rate indicator-acquisition unit 250, a surge-component indicator-acquisition unit 260, and a tail-signal indicator-acquisition unit 270. Each of the indicator-acquisition units operates the calculated information 220 to respectively generate a corresponding indicator message, and the intelligent electronic device 230 is embedded with a descent-rate preset threshold value 310, a surge-component preset threshold value 320, and a tail-signal preset threshold value 330. When each of the indicator messages correspondingly is in compliance with the preset threshold value, the intelligent electronic device 230 determines that the calculated information 220 as a typical molecular binding kinetic curve. With this system configuration, users may recognize the typical molecular binding kinetic curve by using the intelligent electronic device 230 to further understand whether the current system condition or reaction condition functions normally.

The above description is merely illustrative rather than restrictive. Any equivalent modification or alteration without departing from the spirit and scope of the present invention should be included in the appended claims.

What is claimed is:

1. An optical nano-biosensing system, comprising:
a nano-plasmonic sensing device, comprising:
a light-source control circuit;
a sample receiver connected to the light-source control circuit, the sample receiver receiving a sample, and the light-source control circuit generating an incident light from a light source to be projected to the sample receiver;
a light detector detecting an emergent light from the sample receiver to generate a detection signal; and
a signal-amplifying circuit connected to the light detector configured to convert a specific modulation frequency range of the detection signal to generate an amplified signal;
a high-resolution analog-to-digital converter connected to the signal-amplifying circuit configured to digitize the amplified signal to generate a digital signal;
a signal acquisition and processing device connected to the high-resolution analog-to-digital converter and comprising a signal calculator, and the signal calculator configured to operate the digital signal to generate calculated information; and
an intelligent electronic device connected to the signal acquisition and processing device and receiving the calculated information, the intelligent electronic device configured to convert the calculated information to generate sensing output information, and the sensing output information presented on the intelligent electronic device in words, patterns, or a combination thereof.

2. The optical nano-biosensing system according to claim 1, wherein the light-source control circuit further comprises a control circuit and a light-source projector, the control circuit correspondingly generates a light-source driving signal which is then transmitted to the light-source projector according to a feature of the light-source projector, and the light-source projector projects the incident light from the light source having a corresponding wavelength range to the sample receiver according to the light-source driving signal.

3. The optical nano-biosensing system according to claim 1, wherein the voltage-boosting circuit further adjusts the amplified signal, and the amplified signal after voltage boosting is a non-negative value.

4. The optical nano-biosensing system according to claim 1, wherein the sample receiver comprises a nano-plasmonic sensor and a sample vessel; the nano-plasmonic sensor is disposed in the sample vessel; the nano-plasmonic sensor comprises a substrate, a plurality of noble metal nanoparticles, and a plurality of recognition molecules; the plurality of noble metal nanoparticles are disposed on the substrate; one end of each of the recognition molecules is correspondingly disposed on each of the noble metal nanoparticles; the sample vessel accommodates the sample so that the sample is in contact with the nano-plasmonic sensor; a plurality of analyte molecules in the sample bind correspondingly with the other end of each of the recognition molecules; when the nano-plasmonic sensor receives the incident light from the light source, the incident light is absorbed or scattered in the nano-plasmonic sensor; the light detector detects the emergent light from the nano-plasmonic sensor to generate the detection signal.

5. The optical nano-biosensing system according to claim 4, wherein the nano-plasmonic sensor is an optical waveguide-based nano-plasmonic sensor or an optical fiber-based nano-plasmonic sensor.

6. The optical nano-biosensing system according to claim 1, wherein the signal calculator comprises a root-mean-square processor, and the root-mean-square processor operates the digital signal to generate the calculated information according to a root-mean-square algorithm.

7. The optical nano-biosensing system according to claim 1, wherein the signal calculator comprises an absolute-mean processor, and the absolute-mean processor operates the digital signal to generate the calculated information according to an absolute-mean algorithm.

8. The optical nano-biosensing system according to claim 1, further comprising a comb filter, wherein the comb filter is connected to the high-resolution analog-to-digital converter, and the comb filter operates to modify the digital signal.

9. The optical nano-biosensing system according to claim 1, wherein the intelligent electronic device comprises an indicator acquisition processor, the indicator acquisition processor operates the calculated information to generate a plurality of indicator messages, and the intelligent electronic device is embedded with a plurality of preset threshold values; when each of the indicator messages correspondingly is in compliance with each of the preset threshold values, the intelligent electronic device determines that the calculated information as a typical molecular combining kinetic curve.

10. The optical nano-biosensing system according to claim 9, wherein the indicator acquisition processor comprises a descent-rate indicator-acquisition unit, a surge-component indicator-acquisition unit, and a tail-signal indicator-acquisition unit; the plurality of indicator messages comprise a descent-rate indicator message, a surge-component indicator message, and a tail-signal indicator message; the plurality of preset threshold values comprise a descent-rate preset threshold value, a surge-component preset threshold value, and a tail-signal preset threshold value; the descent-rate indicator-acquisition unit operates the calculated information to generate the descent-rate indicator message; the surge-component indicator-acquisition unit operates the calculated information to generate the surge-component indicator message; the tail-signal indicator-acquisition unit operates the calculated information to generate the tail-signal indicator message; the intelligent electronic device determines that the calculated information as the typical molecular binding kinetic curve when the descent-rate indicator message is in compliance with the descent-rate preset threshold value, the surge-component indicator message is in compliance with the surge-component preset threshold value, and the tail-signal indicator message is in compliance with tail-signal preset threshold value.

11. The optical nano-biosensing system according to claim 1, wherein the intelligent electronic device operates the plurality of indicator messages to generate a baseline calibration message according to a baseline algorithm, and the intelligent electronic device calibrates the sensing output information according to the baseline calibration message.

12. The optical nano-biosensing system according to claim 1, further comprising a Bluetooth device, wherein the Bluetooth device is connected to the signal acquisition and processing device and the intelligent electronic device, the signal acquisition and processing device transmits the calculated information to the Bluetooth device, and the Bluetooth device transmits the calculated information to the intelligent electronic device at a remote end.

13. An optical nano-biosensing method for an optical nano-biosensing system comprising a nano-plasmonic sensing device, a high-resolution analog-to-digital converter, a signal acquisition and processing device, and an intelligent electronic device, wherein the nano-plasmonic sensing device further comprises a light-source control circuit, a sample receiver, a light detector, and a signal-amplifying circuit; the signal acquisition and processing device further comprises a signal calculator; the optical nano-biosensing method comprises the following steps:

receiving a sample by the sample receiver;
generating an incident light from a light source to be projected to the sample receiver by the light-source control circuit;
detecting an emergent light from the sample receiver to generate a detection signal by the light detector;
converting a specific modulation frequency range of the detection signal to generate an amplified signal by the signal-amplifying circuit;
digitizing the amplified signal to generate a digital signal by the high-resolution analog-to-digital converter;
operating the digital signal to generate calculated information by the signal calculator of the signal acquisition and processing device; and
receiving the calculated information by the intelligent electronic device and converting the calculated information to generate sensing output information, wherein the sensing output information is presented on the intelligent electronic device in words, patterns, or a combination thereof.

14. The optical nano-biosensing method according to claim 13, wherein the signal calculator comprises a root-mean-square processor, and the root-mean-square processor operates the digital signal to generate the calculated information according to a root-mean-square algorithm.

15. The optical nano-biosensing method according to claim 13, wherein the signal calculator comprises an absolute-mean processor, and the absolute-mean processor operates the digital signal to generate the calculated information according to an absolute-mean algorithm.

16. The optical nano-biosensing method according to claim 13, wherein the intelligent electronic device comprises an indicator acquisition processor, the indicator acquisition processor operates the calculated information to generate a plurality of indicator messages, and the intelligent electronic device is embedded with a plurality of preset threshold values; when each of the indicator messages correspondingly is in compliance with each of the preset threshold values, the intelligent electronic device determines that the calculated information as a typical molecular binding kinetic curve.

17. The optical nano-biosensing method according to claim 16, wherein the indicator acquisition processor comprises a descent-rate indicator-acquisition unit, a surge-component indicator-acquisition unit, and a tail-signal indicator-acquisition unit; the plurality of indicator messages comprise a descent-rate indicator message, a surge-component indicator message, and a tail-signal indicator message; the plurality of preset threshold values comprise a descent-rate preset threshold value, a surge-component preset threshold value, and a tail-signal preset threshold value; the descent-rate indicator-acquisition unit operates the calculated information to generate the descent-rate indicator message; the surge-component indicator-acquisition unit operates the calculated information to generate the surge-component indicator message; the tail-signal indicator-acquisition unit operates the calculated information to generate the tail-signal indicator message; the intelligent electronic device determines that the calculated information as the typical molecular binding kinetic curve when the descent-rate indicator message is in compliance with the descent-rate preset threshold value, the surge-component indicator message is in compliance with the surge-component preset threshold value, and the tail-signal indicator message is in compliance with tail-signal preset threshold value.

18. The optical nano-biosensing method according to claim 16, wherein the intelligent electronic device operates the plurality of indicator messages to generate a baseline calibration message according to a baseline algorithm, and the intelligent electronic device calibrates the sensing output information according to the baseline calibration message.

\* \* \* \* \*